United States Patent [19]

Wolpe et al.

[11] Patent Number: 5,717,074
[45] Date of Patent: Feb. 10, 1998

[54] MACROPHAGE-DERIVED INFLAMMATORY MEDIATOR (MIP-2)

[75] Inventors: Stephen D. Wolpe, Arlington, Mass.; Anthony Cerami, Shelter Island; Barbara Sherry, New York, both of N.Y.

[73] Assignee: The Rockefeller University, New York, N.Y.

[21] Appl. No.: 480,085

[22] Filed: Jun. 7, 1995

Related U.S. Application Data

[62] Division of Ser. No. 285,498, Aug. 3, 1994, which is a continuation of Ser. No. 105,105, Aug. 10, 1993, abandoned, which is a continuation of Ser. No. 914,045, Jul. 13, 1992, abandoned, which is a continuation of Ser. No. 399,971, Sep. 1, 1989, abandoned, which is a continuation-in-part of Ser. No. 240,078, Sep. 2, 1988, abandoned.

[51] Int. Cl.$^6$ .................................................. C07K 16/24
[52] U.S. Cl. .................... 530/388.23; 435/7.24; 435/331; 435/335; 530/387.9; 530/389.2; 530/391.3
[58] Field of Search ................ 435/7.24, 240.27, 435/7.9, 331, 335; 530/388.23, 389.2, 391.3, 387.9

[56] References Cited

U.S. PATENT DOCUMENTS

| | | | |
|---|---|---|---|
| 3,654,090 | 4/1972 | Schuurs et al. | 435/7.93 |
| 3,850,752 | 11/1974 | Schuurs et al. | 435/7.93 |
| 4,603,106 | 7/1986 | Cerami et al. | 435/7.21 |
| 4,961,926 | 10/1990 | Gabrilove | 424/85.1 |
| 5,145,676 | 9/1992 | Fahey, III et al. | 424/85.1 |

FOREIGN PATENT DOCUMENTS

WO 83/00930  3/1983  WIPO.

OTHER PUBLICATIONS

A.M. Campbell, Monoclonal Antibody Technology, Elsevier Science Publishers, B.V., 1984, pp. 1–32.
S.D. Wolpe et al, Proc. Natl. Acad. Sci. USA, 86, 612–616, 1989.
Sherry et al. (1992) Cytokines 4: 117–30.
Sherry et al. (1991) Curr. Opin. Immunol. 3: 56–60.
Widmer et al. (1991) J. Immunol. 146: 4031–40.
Baker et al. (1990) Nucl. Acids Res. 18: 6453.
Dexter et al. (1990) Nature 344: 380–1.
Graham et al. (1990) Nature 344: 442–4.
Haskill et al. (1990) Proc. Natl. Acad. Sci. USA 87: 7732–6.
Davatelis et al. (1989) Science 243: 1066–8.
Wolpe et al. (1989) FASEB J. 3: 2565–73.
Yoshimura et al. (1989) FEBS Letts. 224:487–93.
Kampschmidt, R.F. (1978) J. Ret. Soc. 23:287–97.
Dinarello et al. (1977) Proc. Natl. Acad. Sci. USA 74: 4624–7.
Matsushima et al. (1988) J. Exp. Med. 167: 1883–93.
Peveri et al. (1988) J. Exp. Med. 167: 1547–59.
Van Damme et al. (1988) J. Exp. Med. 167: 1364–76.
Sherry et al. (1988) J. Exp. Med. 168: 2251–9.
Barney et al. (1980) Fever: International Symposium, Dallas TX, Apr. 11–12, 1979. XII+263 P. ISBN 0-89004-451-1(08877) pp. 111–122.
Kampschmidt et al. (1980) J. Lab. Clin. Med. 95: 616–23.
Sipe et al. (1979) J. Exp. Med. 150: 597–606.
Walz et al. (1987) Bioch. Biophys. Res. Comm. 149: 755–61.
Wolpe et al. (1987) in The inhibitors of hamatopoiesis. Najman et al. eds. pp. 197–200.
Yoshimura et al. (1987) J. Immunol. 139: 788–93.
Yoshimura et al. (1987) Proc. Natl. Acad. Sci. USA 84: 9233–7.
Torti et al. (1985) Science 229: 867–9.
Beutler et al. (1985) Science 229: 869–71.
Mahoney et al. (1985) J. Immunol. 134: 1673–1675.
Beutler et al. (1985) Nature 316: 552–4.
Hotez et al. (1984) Parasite Immunol. 6:203–9.
Cochran et al. (1983) Cell 33: 937–47.
Kawakami et al. (1982) Proc. Natl. Acad. Sci. USA: 79: 912–16.

*Primary Examiner*—David Saunders
*Attorney, Agent, or Firm*—Klauber & Jackson

[57] ABSTRACT

An antibody to an inflammatory cytokine is disclosed. The inflammatory cytokine has been isolated from cells that have been incubated with a stimulator material. The inflammatory cytokine is capable of binding to heparin, inducing localized inflammation characterized by polymorphonuclear cell infiltration when administered subcutaneously and having potent in vitro chemotactic activity while inducing little or no in vitro chemokinesis in polymorphonuclear cells, while lacking the ability to suppress the activity of the anabolic enzyme lipoprotein lipase, cause the cytotoxicity of cachectin/TNF-sensitive cells, stimulate the blastogenesis of endotoxin-resistant C3H/HeJ thymocytes, or induce the production of cachectin/TNF by primary thioglycbllate-elicited mouse macrophage cells. A particular inflammatory cytokine has been isolated and its cDNA has been sequenced. The sequence predicts a cDNA of 74 amino acids in length and a molecular weight of 7,908. Diagnostic and therapeutic utilities are proposed, and testing procedures, materials in kit form, recombinant materials and procedures, and pharmaceutical compositions comprising an antibody to the cytokine are likewise set forth.

8 Claims, 7 Drawing Sheets

```
mMIP-2    AVVAS ELRCQCLKT    LPRVDF KNIQSLSVTPPG ........
hPF-4     EAEEDGDLQCLCVKT    TSQVRPRHITSLEVIKAG .........
bPF-4     EAEEDGEDLQCVCLKT    TSGINPRHITSLEVIKAG .........
rPF-4     VTRASPEESDGDLSCVCVKT    SSRIHLKRITSLEVIKAG .........
hPBP      SSTKGQTKRNLAKGKEESLDSDLYAELRCMCIKT    TSGIHPKNIQSLEVIGKG .........
hNAP-1    AVLPRSAKELRCQCIKT    YSKPFHPKFIKELRVIESG .........
hIP10     VPLSRTVRCTCISI      SNQPVNPRSLEKLEIIPAS ........
c9E3      ALSQGRTLVKMGNELRCQCIST    HSKFIHPKSIQDVKLTPSG .........
hGro      RRAAGASVATELRCQCLQT    LQGIHPKNIQSVNVKSPG ........
hamGro    RLATGAPVANELRCQCLQT    MTGVHLKNIESLKVTPPG ........
mKC       RLATGAPIANELRCQCLQT    MAGIHLKNIQSLKVLPSG ........
```

FIG. 2

|         | bPF-4 | rPF-4 | hPBP | c9E3 | hNAP-1 | hIP10 | hGro | hamGro | mKC  | mMIP-2 |
|---------|-------|-------|------|------|--------|-------|------|--------|------|--------|
| hPF-4   | 68.7  | 65.6  | 53.5 | 26.6 | 39.2   | 37    | 33.3 | 37     | 33.3 | 39.2   |
| bPF-4   | --    | 60    | 66.6 | 30   | 39.2   | 33.3  | 44.4 | 39.2   | 42.8 | 40.7   |
| rPF-4   |       | --    | 55.1 | 33.3 | 46.4   | 32.1  | 39.2 | 42.8   | 46.4 | 41.3   |
| hPBP    |       |       | --   | 53.5 | 57.1   | 32.1  | 60.7 | 55.5   | 62.9 | 53.5   |
| c9E3    |       |       |      | --   | 50     | 27.2  | 48.3 | 48.3   | 54.8 | 41.9   |
| hNAP-1  |       |       |      |      | --     | 26.6  | 46.6 | 46.6   | 50   | 46.6   |
| hIP10   |       |       |      |      |        | --    | Ins. | Ins.   | Ins. | Ins.   |
| hGro    |       |       |      |      |        |       | --   | 65.6   | 65.6 | 62.5   |
| hamGro  |       |       |      |      |        |       |      | --     | 81.2 | 68.7   |
| mKC     |       |       |      |      |        |       |      |        | --   | 59.3   |

F I G. 3

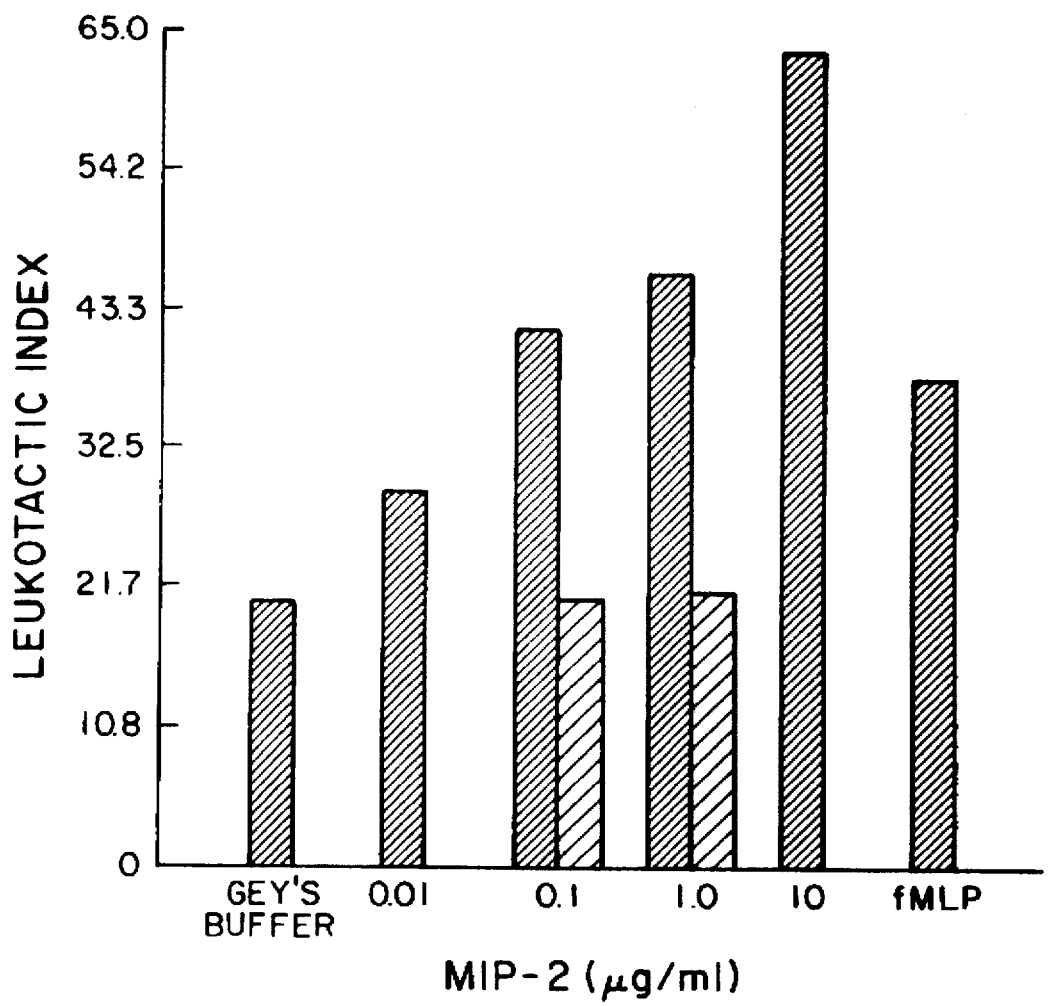
F I G. 5

ALA VAL VAL ALA SER GLU LEU ARG CYS GLN CYS LEU LYS THR LEU PRO
ARG VAL ASP PHE LYS ASN ILE GLN SER LEU SER VAL THR PRO PRO GLY

FIG. 6

```
                                                               -26
                                                               Met
               GCTTCCTCGGGCACTCCAGACTCCAGCCACACTTCAGCCTAGCGCC ATG

-20
Ala Pro Pro Thr Cys Arg Leu Leu Ser Ala Ala Leu Val Leu Leu
GCC CCT CCC ACC TGC CGG CTC CTC AGT GCT GCA CTG GTC CTG CTG

-10                                           1
Leu Leu Leu Ala Thr Asn His Gln Ala Thr Gly Ala Val Val Ala
CTG CTG CTG GCC ACC AAC CAC CAG GCT ACA GGG GCT GTT GTG GCC 10                                    20
Ser Glu Leu Arg Cys Gln Cys Leu Lys Thr Leu Pro Arg Val Asp
AGT GAA CTG CGC TGT CAA TGC CTG AAG ACC CTG CCA AGG GTT GAC

30
Phe Lys Asn Ile Gln Ser Leu Ser Val Thr Pro Pro Gly Pro His
TTC AAG AAC ATC CAG AGC TTG AGT GTG ACG CCC CCA GGA CCC CAC 40                                    50
Cys Ala Gln Thr Glu Val Ile Ala Thr Leu Lys Gly Gly Gln Lys
TGC GCC CAG ACA GAA GTC ATA GCC ACT CTC AAG GGC GGT CAA AAA

60
Val Cys Leu Asp Pro Glu Ala Pro Leu Val Gln Lys Ile Ile Gln
GTT TGC CTT GAC CCT GAA GCC CCC CTG GTT CAG AAA ATC ATC CAA 70              74
Lys Ile Leu Asn Lys Gly Lys Ala Asn OP
AAG ATA CTG AAC AAA GGC AAG GCT AAC TGA CCTGGAAAGGAGGAGCCTGGG

CTGCTGTCCCTCAACGGAAGAACCAAAGAGAAAGAAAAAAACAAACAGCACCCGGGAAGC

CTGGATCGTACCTGATGTGCCTCGCTGTCTGAGAGTTCACTTATTTATTTATCTATGTAT

TTATTTATTTATTAATTCCATTGCCCAGATGTTGTTATGTTTATTATGATATTTAAAGAT

ATCGATTCGCTAATTCACTGTAATATCTTAAAAGGTCATTTTAATATGTTAAAGTTTATT

TTAATAATGTTTAATGTGTTCAATTAAAGTTATTTAACTTATATAGTTGGAAGGTGATAC

ATTTTTAAACCTATTTATTCATTAGTTTCTGGGGAGAGGGTGAGTTGGGAACTAGCTACA

TCCCACCCACACAGTGAAAGAGACTGGGGATAAGGGGTGGGGGTGGGGACAAATAGATGC

AGTCGGATGGCTTTCATGGAAGTAGTGTGCATGTTCACATCATTTTTTTGTAAGCACCGA

GGAGAGTAGAACAGCTGTTATTTAGGTTTCAGTGTTTGTAAACTGTATGTACAACATTTT

TGATGCTGGATTTCAATGTAATGTTGTGAGTAACCCTTGGACATTTTATGTCTTCCTCGT

AAGGCACAGTGCCTTGCTTAGCAATTGTTTTGTCATGCCTTTTCGTGTCTTGAAGTGGAC

ACATTTATTTATTCATGTATTTTTACAAATAACAAAAAATAAAAACGTCTGTTAAAAAAA

AAAAAAAAAAAAAAAAAAA            F I G. 7
```

MACROPHAGE-DERIVED INFLAMMATORY MEDIATOR (MIP-2)

The present application is a division of application Ser. No. 08/285,498, filed Aug. 3, 1994, which is a continuation of Ser. No. 08/105,105, filed Aug. 10, 1993, now abandoned, which is a continuation of Ser. No. 07/914,045, filed Jul. 13, 1992, now abandoned, which is a continuation of Ser. No. 07/399,971, filed Sep. 1, 1989, now abandoned, which is a continuation-in-part of Ser. No. 07/240,078, filed Sep. 2, 1988, now abandoned.

RELATED PUBLICATIONS

The Applicants are authors or co-authors of several articles directed to the subject matter of the present invention. These articles supplement those articles listed in U.S. Pat. No. 4,603,106, which earlier articles are incorporated herein by reference. (1) [Applicant Cerami co-authored with B. Beutler, J. Mahoney, N. Le Trang and P. Pekala] "Purification of Cachectin, a Lipoprotein Lipase-Suppressing Hormone Secreted By Endotoxin-Induced RAW 264.7 Cells", J. EXP. MED. 161:984–995 (May, 1985); (2) [Applicant Cerami co-authored with M. Kawakami, J. R. Mahoney, N. Le Trang, W. Vine, and Y. Ikeda] "Lipopolysaccharide-Treated RAW 264.7 Cells Produce a Mediator Which Inhibits Lipoprotein Lipase in 3T3-L1 Cells", J. IMMUNOL. 134 (3):1673–1675 (March, 1985); (3) [Applicant Cerami co-authored with P. J. Hotez, N. Le Trang, and A. H. Fairlamb] "Lipoprotein Lipase Suppression in 3T3-L1 Cells by a Haematoprotozoan-Induced Mediator From Peritoneal Exudate Cells.", PARASITE IMMUNOL. (Oxf.) 6:203 (1984); (4) [Applicant Cerami co-authored with B. Beutler, D. Greenwald, J. D. Hulmes, M. Chang Y.-C.E. Pan, J. Mathison and R. Ulevitch] "Identity of Tumor Necrosis Factor and Macrophage-Secreted Factor Cachectin", NATURE 316:552–554 (1985); (5) [Applicant Cerami co-authored with B. Beutler, F. M. Torti, B. Dieckmann and G. M. Ringold] "A Macrophage Factor Inhibits Adipocyte Gene Expression: An In Vitro Model of Cachexia", SCIENCE 229:867–869 (1985); (6) [Applicant Cerami co-authored with B. Beutler and I. W. Milsark] "Passive Immunization Against Cachectin/Tumor Necrosis Factor (TNF) Protects Mice From the Lethal Effect of Endotoxin", SCIENCE 229:869–871 (1985); (7) [Applicants Cerami, Wolpe and Sherry co-authored with B. Beutler, G. Davatelis, D. G. Hesse, H. T. Nbuyen, L. I. Moldawer, C. F. Nathan and S. F. Lowry], "Macrophages Secrete a Novel Heparin-Binding Protein with Inflammatory and Neutrophil Chemokinetic Properties", J EXP. MED 167:570–581 (1988); (8) [Applicants Wolpe, Cerami and Tekamp-Olson co-authored with G. Davatelis, K. Hermsen, C. Luedke, C. Gallegos, D. Coit and J. Merryweather], "Cloning and Characterization of a cDNA for Murine Macrophage Inflammatory Protein (MIP), A Novel Monokine with Inflammatory and Chemokinetic Properties", J EXP. MED., 167:1939–1944 (June, 1988); (9) [Applicants co-authored with C. Gallegos, D. Bauer, G. Davatelis, F. Masiarz and D. Coit], "Resolution of the Two Components of Macrophage Inflammatory Protein 1, and Cloning and Characterization of One of Those Components, MIP-1β", J EXP MED. 168:2251–2259 (December, 1988); and (10) [Applicants Wolpe, Cerami and Sherry co-authored with D. Juers, G. Davatelis, and R. Yurt], "Identification and Characterization of Macrophage Inflammatory Protein 2", PROC. NATL. ACAD. SCI. USA 86:612–616 (January, 1989). All of the above listed articles are incorporated herein by reference.

The research leading to the present invention was funded in part by grants from the National Institutes of Health and the Rockefeller Foundation.

BACKGROUND OF THE INVENTION

The present invention is generally directed to materials and associated methods for the analysis and treatment of the effects and corresponding operation of invasive stimuli such as infection upon animal hosts, and in particular, is concerned with the identification of materials which may participate in the host response to such invasive stimuli.

Several common physiological and biochemical derangements have been observed in various mammalian hosts responding to a variety of invasive stimuli such as bacterial, viral, or protozoal infection; tumors; or endotoxemia; as well as in idiopathic states. For example, these responses include fever, leukocytosis, hyperlipidemia, reduced food intake (anorexia), reduced activity, wasting (cachexia), and other modifications in muscle, white blood cell and liver metabolism. In particular, recent studies aimed at elucidating the biochemical mechanism of cachexia in rabbits infected with *Trypanosoma brucei* noted that animals with a minimal parasite burden became moribund and exhibited an extreme hypertriglyceridemia, with a marked elevation of plasma very low density lipoprotein (VLDL). See C. A. Rouser and A. Cerami, MOL. BIOCHEM. PARASITOL. 1:31–38 (1980). The hyper-triglyceridemic state was remarkable in view of the severe wasting diathesis that accompanied this experimental infection. The elevation of plasma VLDL was shown to result from a clearing defect, caused by a loss of peripheral tissue lipoprotein lipase (LPL) activity.

Reduced LPL activity has been observed by others, and it has been noted that this condition has existed when the human body was in shock. See E. B. Man, et al., "The Lipids of Serum and Liver in Patients with Hepatic Diseases", CLIN. INVEST 24 at 623, et seq (1945); See also John I Gallin, et al , "Serum Lipids in Infection", N. ENGL. J. MED. 281 at 1081–1086 (Nov. 13, 1969); D. Farstchi, et al., "Effects of Three Bacterial Infections on Serum Lipids of Rabbits", J BACTERIOL. 95 at 1615, et seq. (1968); S. E. Grossberg, et al., "Hyperlipaemia Following Viral Infection in the Chicken Embryo: A New Syndrome", NATURE (London) 208 at 954, et seq. (1965); Robert L. Hirsch, et al., "Hyperlipidemia, Fatty Liver and Bromsulfophthalein Retention in Rabbits Injected Intravenously with Bacterial Endotoxin", J. LIPID. RES. at 563–568 (1964); and Osamu Sakaguchi, et al., "Alternations of Lipid Metabolism in Mice Injected With Endotoxins", MICROBIOL. IMMUNOL. 23 (2) at 71–85 (1979); R. F. Kampschmidt, "The Activity of Partially Purified Leukocytic Endogenous Mediator in Endotoxin Resistant C3H/HeJ Mice", J. LAB CLIN. MED 95 at 616, et seq. (1980); and Ralph F. Kampschmidt, "Leukocytic Endogenous Mediator", J. RET. SOC. 23 (4) at 287–297 (1978).

Additionally, publications are known by the Applicants that discuss the identification and existence of "mediators" that appear to be involved in the host response to infection; and in particular, the following articles, the texts of which are incorporated herein by reference, are listed: Sipe, J. D., et al., J. EXP. MED., 150:597–606 (1979); and Barney, C. C., et al., LIPTON, J. M. (Ed.), FEVER: INTERNATIONAL SYMPOSIUM, Dallas, Tex., Apr. 11–12, 1979 XII+263P. Raven Press: New York. Illus. ISBN 0-89004-451-1 (08877), 0 (0), pp.111–122 (1980); and Dinarello, C. A., "Human Leukocytic Pyrogen: Purification and Development of a Radioimmunoassay", PROC. NATL. ACAD. SCI. USA, 74(10) at 4624–4627 (October, 1977). All of the factors identified and investigated by each of the authors in the above noted articles and the articles authored or co-authored by Kampschmidt have been determined to comprise a single grouping of factors which has been identified as interleukin-1 (IL-1). This determination has been documented in an article by Charles A. Dinarello, published in REVIEWS OF INFECTIOUS DISEASES, at Volume 6, No. 1 (January–February, 1984), the text of which is also incorporated herein by reference.

A similar deficiency of LPL activity was noted by Applicants in C3H/HeN mice after administration of Escherichia coli lipopolysaccharide (LPS). In contrast, the loss of LPL activity was not demonstrable in C3H/HeJ mice, which are genetically resistant to LPS. This resistance to endotoxin-induced LPL deficiency could be circumvented by the administration of serum obtained from endotoxin-sensitive animals that had been injected with LPS two hours previously. Similarly, resistance could be overcome by injecting conditioned medium from endotoxin-stimulated thioglycollate-elicited peritoneal macrophages, obtained from sensitive mice. These findings were set forth in full detail in application Ser. No. 414,098, now U.S. Pat. No. 4,603,106, the disclosure of which is incorporated herein by reference.

The above work was prompted by the belief that the "mediator" or "mediators" existed and were suspected to have a significant effect upon general anabolic activity of energy storage cells in the animal host. It was suspected that such "mediator" exerted a depressive effect upon the activity of certain anabolic enzymes, whose reduced activity was observed for instance, where the hosts enter the condition known as shock, as in response to infectious invasion. Resultingly, the relationship of the mediator produced by endotoxin-stimulated peritoneal mouse exudate cells, upon endotoxin-sensitive and endotoxin-insensitive mice alike, and the development through such investigation of a reagent for the measurement of anabolic enzyme activity was set forth in first filed abandoned application Ser. No. 299,932, incorporated herein by reference.

Further investigation of this system was made in conjunction with the 3T3-L1 "preadipocyte" model system, and the corresponding development of methods and associated materials for the development of antibodies to the "mediator" and other diagnostic procedures was then set forth in application Ser. No. 351,290, also incorporated herein by reference and now abandoned. Thereafter, in subsequent application Ser. No. 414,098, now U.S. Pat. No. 4,603,106, it was established that the mediator substance derived from the endotoxin stimulation of macrophage cells exhibited the activities of suppressing the anabolic enzymes lipoprotein lipase, acetyl Coenzyme A Carboxylase and fatty acid synthetase, and further, inhibited the growth and differentiation of erythroid-committed cells.

Additional work set forth in articles (1) and (4) by Beutler et al., and application Sr. No. 766,852, now abandoned, the disclosure of which is incorporated herein by reference, has resulted in the discovery that the earlier identified mediator substance contained a further protein component which possesses a number of activities, which distinguished it from both the mediator substance and the other factors identified in the art and known as interleukin-1 and interleukin-2. Further work set forth in articles (7)–(9) and Parent Application Ser. No. 104,827, now abaondoned, the disclosure of which is incorporated herein by reference, established the presence of an additional factor (MIP-1) in the mediator substance which factor demonstrates a distinguishable profile of activities.

Subsequently, the present inflammatory cytokine MIP-2 was isolated and purified and its distinctive activities elucidated as set forth in immediate Parent Application Ser. No. 240,078 and now abandoned. Since that time, the complete sequence of the present cytokine has been determined following the cloning of its cDNA, and expression of the cytokine has been pursued. The present application is intended to include the additional information regarding this cytokine that is now available as a result of the investigations of the inventors herein.

MIP-2 is a member of a homologous multigene family. Members of this family that have highest homology in protein sequence (generally predicted from cloned cDNA) include MGSA and KC. MGSA (Richmond et al., EMBO J. 7: 2025 (1988) is an autocrine growth factor with potent mitogenic activity secreted by human melanoma cells and is the product of the human gro gene (Anisowicz et al., PROC. NAT. ACAD. SCI. USA 84:7188 (1987). MGSA has 61.6% identity in amino acid sequence to MIP-2; the predicted protein sequence of the hamster homolog of MGSA has 68.4% identify to MIP-2. The murine KC gene product is induced by PDGF and is thought to be the murine homolog of the human MGSA/gro gene (66.3% amino acid identity to MIP-2).

The present applicants know of no prior art on the expression of recombinant MIP-2 although Lipes et al., (PROC. NATL. ACAD. USA 85: 9704, 1988) described baculovirus expression of Act-2 cDNA, a putative human homolog of murine MIP-1β, to show that the protein encoded was secreted and to identify the mature N-terminal sequence.

Members of the MIP-1 and MIP-2 gene families have been expressed but the pertinence of these results to MIP-2 expression is questionable. The literature is summarized as follows. JE, a cDNA that encodes a protein with homology to MIP-1α and MIP-1β, has been expressed in COS-1 cells to confirm that it encodes a polypeptide core of about 12 kDa (Rollins et al., PROC. NATL. ACAD. SCI. USA 85: 3738, 1988). KC, a cDNA that encodes a protein with homology to MIP-2, has been expressed in COS-1 cells to show that it encodes a secreted protein by Oguendo et al., J. BIOL. CHEM. 264:4133 (1989). Connective tissue activating peptide-III (CTAP) reported by Mullenbach et al., J. BIOL. CHEM. 261:719 (1986) and IP-10, reported by Luster and Ravetch, J. EXP. MED. 166:1084 (1987) both members of the MIP-2 gene family, have been expressed as an α-factor fusion in yeast and in E. coli., respectively. Finally, Lindley et al., PROC. NAT. ACAD. SCI. USA 85:9199 (1985) have expressed NAF, a member of the MIP-2 family, in E. coli. After purification and renaturation, this recombinant protein was found to have the same bioactivity identified for the native molecule.

SUMMARY OF THE INVENTION

In accordance with the first aspect of the present invention, the inflammatory cytokine MIP-2 isolated from the mediator substance is disclosed, and comprises a protein that has been purified and is cationic under basic physiological conditions. The inflammatory cytokine of the present invention exhibits the ability to bind to heparin, even at high salt concentrations, to induce localized inflammation characterized by polymorphonuclear cell infiltration when administered subcutaneously and is an extremely active chemotactic agent while inducing little or no chemokinetic activity. The present inflammatory cytokine however, lacks certain activities common to other factors that have been isolated from the mediator substance disclosed in U.S. Pat. No. 4,603,106.

In particular, the present inflammatory cytokine lacks the ability to suppress the activity of the anabolic enzyme lipoprotein lipase (LPL), and is unable to cause the cytotoxicity of cachectin/TNF-sensitive L929 cells, to stimulate the blastogenesis of endotoxin-resistant C3H/HeJ thymocytes, or to induce the production of cachectin/TNF by primary thioglycollate-elicited mouse macrophage cells. These latter characteristics all absent from the present inflammatory cytokine are exhibited by the known factors cachectin/TNF and interleukin-1 (IL-1), and thereby distinguish the present inflammatory cytokine therefrom.

The most significant affirmative activities exhibited by the present inflammatory cytokine appear to be the ability to bind to heparin and the ability to induce localized inflammation characterized by polymorphonuclear (PMN) cell infiltration. Accordingly, while the exact role that the present isolate plays in the cascade of reactions to host invasion is as yet undefined, its participation in the elicitation of certain of the activities and conditions associated with mobilization against host invasion is clear. Accordingly, the inflammatory cytokine possesses the potential for use as a diagnostic tool to identify and perhaps differentiate between various stimuli whether invasive or idiopathic, by the activation of the present inflammatory cytokine that such stimuli may promote.

The present inflammatory cytokine was initially identified and characterized and found to contain a single chain, 6 kilodalton protein on sodium dodecyl sulfate (SDS-PAGE) which migrates on gel filtration as a monomer or dimer. Partial N-terminal amino acid sequence data as depicted in FIG. 2 revealed that MIP-2 is a member of a family of cytokines, the archetype of which is platelet factor 4 ($PF_4$).

As set out above, the present inflammatory cytokine may be prepared by the stimulation of macrophage cells with a material that accompanies an invasive stimulus. In particular, a sample of macrophage cells which may be derived from a variety of sources may be incubated with a stimulator material such as endotoxin or trypanosomes, to produce the mediator substance disclosed in U.S. Pat. No. 4,603,106. Such incubation may take place for a period of time of up to twenty hours, and exact time limits will vary with the particular cells selected for incubation.

Further properties of the present inflammatory cytokine include its inability to induce fever in rabbits, or to induce superoxide formation or a respiratory burst in human neutrophils in vitro.

Following such incubation, the medium may be appropriately treated as by centrifuging, to recover a supernatant containing the crude mediator substance. The mediator substance may then be further treated as by filtration or precipitation. Thereafter, the crude mediator substance may be subjected to a series of known isolation techniques, whereupon the inflammatory cytokine may be recovered. The present invention naturally contemplates alternate means for preparation of the inflammatory cytokine, including where applicable known genetic replicative techniques, and the invention is accordingly intended to cover such synthetic preparations within its scope.

As noted above, the present invention also includes a purified protein having the above-noted activities and characteristics, that displays the $NH_2$-terminal partial amino acid consensus sequence set forth in FIG. 6, as determined in mice. The cDNA for MIP-2 has been cloned and, as set forth in FIG. 7, predicts a mature protein of 74 amino acids in length with a molecular weight of 7908 and a translated molecular weight of 10,622.52 for the precursor peptide.

Accordingly, the present invention also includes the identification of the purified peptide comprising the present cytokine that exhibits the above noted activities and characteristics, and that displays the mature amino acid sequence set forth below and in FIG. 7, as determined in mice.

GLY ALA VAL VAL ALA SER GLU LEU ARG CYS GLN CYS LEU LYS THR LEU PRO ARG VAL ASP PHE LYS ASN ILE GLN SER LEU SER VAL THR PRO PRO GLY PRO HIS CYS ALA GLN THR GLU VAL ILE ALA THR LEU LYS GLY GLY GLN LYS VAL CYS LEU ASP PRO GLU ALA PRO LEU VAL GLN LYS ILE ILE GLN LYS ILE LEU ASN LYS GLY LYS ALAASN

As stated earlier, the foregoing sequence bears no striking similarity to any of the known factors and accordingly establishes that the present inflammatory cytokine is distinguishable therefrom. The isolation of the above cDNA amino acid sequence facilitates the reproduction of this cytokine by recombinant genetic techniques as discussed in detail hereinafter. Thus, the invention provides the DNA sequence encoding the present inflammatory cytokine or analogs thereof, which may be used to construct vectors for expression in host systems by recombinant DNA techniques.

The invention further includes a method for detecting idiopathic or invasive stimuli on the basis of their ability to elicit the activities affected by the present inflammatory cytokine. In particular, invasive stimuli could be identified and detected by their ability to induce a material which is able to bind to heparin and to induce localized inflammation with neutrophil infiltration and chemotacticity. In this method, macrophage cells derived for example, from the RAW 264.7 cell line could be treated with/exposed to a number of known stimulator materials such as endotoxin, trypanosomes or the like, as a control, while parallel cellular samples could be treated with or exposed to an extract of material from the presumed situs of the infective stimulus. All samples could thereafter be incubated in accordance with the methods described above, and thereafter subjected to the sequence of separation techniques also defined, whereupon testing of the resulting isolates derived from the control and unknown samples could be compared to determine whether the inflammatory cytokine, if any, developed is identical or even similar.

In similar fashion, an assay system for screening of potential drugs effective to counteract the inflammatory cytokine may be prepared. In one instance, the test drug could be administered to a stimulated macrophage sample to determine its effect upon the production of the inflammatory cytokine. In an alternate procedure, the inflammatory cytokine may be introduced into a cellular test system in which the cytokine is known to be active, and the prospective drug may also be introduced to the same cell culture and the culture may thereafter be examined to observe any changes in the activity of the inflammatory cytokine in comparison with the addition of the prospective drug alone, or the effect of added quantities of the known inflammatory cytokine.

The present invention also relates to a method for detecting the presence of stimulated, spontaneous, or idiopathic pathological states in mammals, by measuring the activity and presence of the inflammatory cytokine of the present invention. More particularly, the activity of the inflammatory cytokine may be followed directly by the assay techniques discussed later on, through the use of an appropriately labeled quantity of the cytokine. Alternately, the cytokine can be used to raise binding partners or antibodies that could in turn, be labeled and introduced into a medium such as serum, to test for the presence of inflammatory cytokine therein, and to thereby assess the state of the host from which the medium was drawn.

Thus, both the inflammatory cytokine and any antibodies that may be raised thereto, are capable of use in connection with various diagnostic techniques, including immunoassays, such as a radioimmunoassay, using for example, an antibody to the inflammatory cytokine that has been labeled by either radioactive addition, reduction with sodium borohydride, or radioiodination.

In an immunoassay, a control quantity of the inflammatory cytokine, its antibody, or the like may be prepared and labeled with an enzyme, a specific binding partner and/or a radioactive element, and may then be introduced into a blood sample of a mammal believed to be undergoing invasion. After the labeled material or its binding partner(s) has had an opportunity to react with sites within the sample, the resulting mass may be examined by known techniques, which may vary with the nature of the label attached.

In the instance where a radioactive label, such as the isotopes $^{14}C$, $^{131}I$, $^{3}H$, $^{125}I$ and $^{35}S$ are used, known currently available counting procedures may be utilized. In the instance where the label is an enzyme, detection may be accomplished by any of the presently utilized colorimetric, spectrophotometric, fluorospectro-photometric or gasometric techniques known in the art. The present invention includes an assay system which may be prepared in the form of a test kit for the quantitative analysis of the extent of the presence of the inflammatory cytokine. The system or test kit may comprise a labeled component prepared by one of the radioactive and/or enzymatic techniques discussed herein, coupling a label to the inflammatory cytokine; and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the inflammatory cytokine, antibodies to the inflammatory cytokine, or upon agents or other drugs determined to possess the same or an antagonistic activity. A first therapeutic method is associated with the prevention of the manifestations of the activities of the inflammatory cytokine in mammals, such as inflammation and fever, and comprises administering either an antibody to the cytokine, an agent capable of modulating the production and/or activity of the cytokine, or an agent not an antibody to the cytokine that is capable of acting as an antagonist to the cytokine, either individually or in mixture with each other in an amount effective to prevent the development of those conditions in the host.

More specifically, the therapeutic method generally referred to herein could include the method for the treatment of inflammation and fever by the administration of pharmaceutical compositions that may comprise effective quantities of antibodies to the inflammatory cytokine, or other equally effective drugs developed for instance by a drug screening assay prepared and used in accordance with a further aspect of the present invention.

A variant embodiment of this therapeutic method could include initially detecting the presence and activity of the inflammatory cytokine and thereafter administering the appropriate pharmaceutical composition.

A second therapeutic method seeks to take advantage of the inflammatory activity of the cytokine and in particular, its ability to cause the movement and mobilization of neutrophils in response to invasive stimuli such as infection. Accordingly, the inflammatory cytokine may be prepared in a suitable formulation for administration to the situs of infection which for example, may develop where tissue trauma has occurred. In such instance, the inflammatory cytokine may be prepared in a sterile solution and delivered to the trauma or wound as part of an irrigation fluid or by direct dosage such as, in a pharmaceutical composition, the latter course of administration contemplating topical and parenteral routes. Naturally, the inflammatory cytokine may be used to raise equally effective agents or drugs by known methods that may then be formulated into pharmaceutical compositions suitable for administration in the same manner and for the same purpose as for the inflammatory cytokine itself.

Accordingly, it is a principal object of the present invention to provide an inflammatory cytokine in purified form that exhibits certain characteristics and activities associated with the host response to invasive stimuli in mammals.

It is a further object of the present invention to provide methods for the preparation of the inflammatory cytokine, including recombinant means.

It is a further object of the present invention to provide a method for detecting the presence of the inflammatory cytokine in mammals in which invasive, spontaneous, or idiopathic pathological states such as infection are suspected to be present.

It is a further object of the present invention to provide a method and associated assay system for screening substances such as drugs, agents and the like, potentially effective in either mimicking the activity or combating the adverse affects of the inflammatory cytokine in mammals.

It is a still further object of the present invention to provide a method for the treatment of mammals to control the amount or activity of the inflammatory cytokine, so as to alter the adverse consequences of such presence or activity.

It is a still further object of the present invention to provide a method for the treatment of mammals to promote the amount or activity of the inflammatory cytokine, so as to treat or avert the adverse consequences of invasive, spontaneous or idiopathic pathological states.

It is a still further object of the present invention to provide pharmaceutical compositions for use in therapeutic methods which comprise or are based upon the inflammatory cytokine or its binding partner(s), or upon agents or drugs that control the production, or that mimic or antagonize the activities of the inflammatory cytokine.

Other objects and advantages will become apparent to those skilled in the art from a review of the ensuing description which proceeds with reference to the following illustrative drawings.

BRIEF DESCRIPTION OF THE DRAWINGS

FIG. 2 depicts the partial $NH_2$-terminal amino acid sequences of MIP-2 and other members of the platelet factor 4 family. Sequences were obtained from the literature and aligned via a conserved cysteine residue. PBP (platelet basic protein) is the precursor for β-thromboglobulin and CTAP III. Amino acids enclosed in boxes are conserved between the various members of the platelet factor 4 family. Lower case prefixes refer to species: m=murine, h=human, b=bovine, r=rat, c=chicken, ham=hamster.

FIG. 3 is a table showing a comparison of the percent sequence identity over the region corresponding to the partial $NH_2$-terminal amino acid sequence obtained for MIP-2. Sequences were compared using the FASTP program. Comparisons are only for the portion of each sequence corresponding to that available for MIP-2 as aligned in FIG. 2. Ins.=Insignificant.

FIG. 5 is a graphical depiction of human polymorphonuclear chemotaxis and chemokinesis in response to MIP-2. Chemotaxis (darkened bars) was measured by introducing MIP-2 into the lower well of the chamber only. Chemokinesis (lightened bars) was measured by introducing the same concentration of MIP-2 into the upper and lower chambers. fMet-Leu-Phe (fMLP) was used at a concentration of $10^{-8}$ M.

FIG. 6 is a depiction of the partial N-terminal sequence of the inflammatory cytokine of the present invention.

FIG. 7 depicts the complete nucleotide sequence of a cDNA clone for MIP-2. The predicted translated molecular weight of the precursor peptide is 10,622.52. The mature peptide sequence, starting at position one, is 74 amino acids in length.

DETAILED DESCRIPTION

Figure 1:
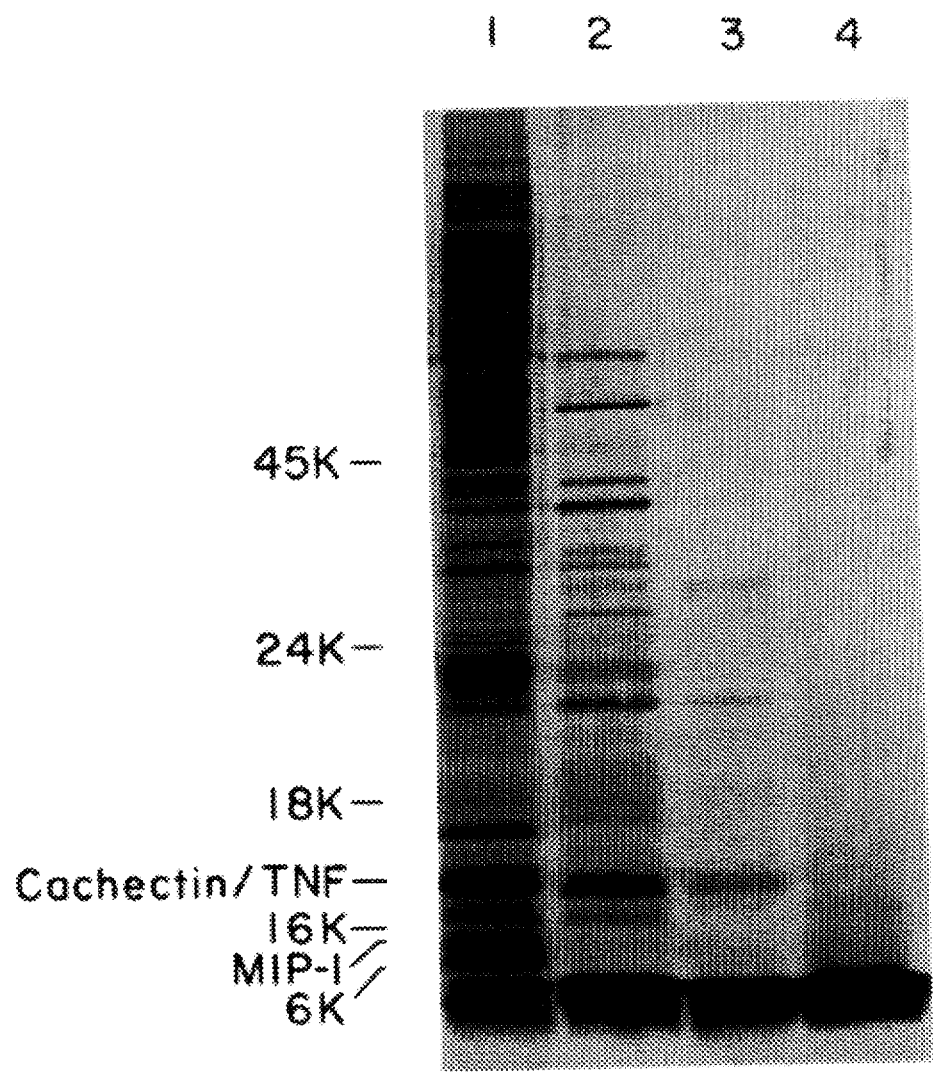
FIG. 1 is an electrophoretic gel depiction of the purification of MIP-2. The final positions of the molecular weight markers (in kilodaltons) are shown on the left along with the positions of cachectin/TNF and MIP-1 in this 10–18% $NaDodSO_4$-PAGE system. The four lanes show successive stages of purification of MIP-2: Lane 1-concentrated and diafiltrated crude supernatant from RAW 264.7 cells; Lane 2-effluent from Mono Q (anion exchange) column chromatography of RAW 264.7 supernatant; Lane 3—pooled peak fractions after purification on heparin-Sepharose; Lane 4—pure MIP-2 fractions after purification on Superose 12 (gel filtration).

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984).

Therefore if appearing herein, the following terms shall have the definitions set out below.

The term "stimulus" and its plural as used herein are intended to apply to invasive events such as infection, as well as conditions caused by wounding, and to idiopathic or spontaneous states that may for example, originate from cellular or metabolic derangements or other causes.

The terms "inflammatory cytokine", "macrophage inflammatory protein 2" and "MIP-2" as used throughout the present application and claims refer to protein material having the partial N-terminal sequence data presented in FIGS. 2 and 6, the mature peptide sequence presented in FIG. 7, and the profile of activities set forth herein and in the Claims. Accordingly, proteins having similar sequences to those set forth herein but dispiaying substantially equivalent or altered activity are likewise contemplated. These modifications may be deliberate, for example, such as modifications obtained through site-directed mutagenesis, or may be accidental, such as those obtained through mutations in hosts that are MIP-2 producers. Also, the terms "inflammatory cytokine", "macrophage inflammatory protein 2" and "MIP-2" are intended to include within their scope the proteins specifically recited herein as well as all substantially homologous analogs and allelic variations.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes. For instance, alpha-factor, a native yeast protein, is secreted from yeast, and its signal sequence can be attached to heterologous proteins to be secreted into the media (See U.S. Pat. No. 4,546,082, EPO 0 116 201, publication date 12 Jan. 1983; U.S. Patent application Ser. No. 522,909, filed 12 Aug. 1983 and now abandoned). Further, the alpha-factor leader and its analogs have been found to secrete heterologous proteins from a variety of yeast, such as Saccharomyces and Kluyveromyces, (EPO 88312306.9 filed 23 Dec. 1988; U.S. Patent application Ser. No. 139,682, filed 30 Dec. 1987, and EPO Pub. No. 0 301 669, publication date 1 Feb. 1989).

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

An "antibody" is any immunoglobulin, including antibodies and fragments thereof, that binds a specific epitope. The term encompasses, inter alia, polyclonal, monoclonal, and chimeric antibodies, the last mentioned described in further detail in U.S. Pat. Nos. 4,816,397 and 4,816,567.

Intron-free DNA provided by the present invention is novel, since it is believed that the naturally-occurring human genes contain introns. Hence, the term "intron-free" excludes the DNA sequences which naturally occur in the chromosomes of human or bovine cells. The present invention also encompasses the intron-free cDNA sequences derivable from the DNA sequences disclosed herein.

In its primary aspect, the present invention concerns the isolation and identification of a newly discovered particular factor hereinafter referred to as the inflammatory cytokine, macrophage inflammatory protein 2 or MIP-2, that has been found to be present in macrophages or macrophage cell lines that are stimulated by materials referred to herein as stimulator materials, that characteristically accompany an invasive stimulus, such as bacteria, virus, certain tumors, protozoa and other toxins such as endotoxin, or an idiopathic state. As with the mediator substance disclosed in U.S. Pat. No. 4,603,106, the present inflammatory cytokine, which has been determined to be a component of the former mediator substance, appears to be capable of causing certain conditions such as inflammation to develop in the tissues of a mammal, which reflect the reaction of a mammal in a stimulated or spontaneous pathological state.

In particular, the inflammatory cytokine appears to be capable of inducing localized inflammation when administered subcutaneously which inflammation is characterized by polymorphonuclear cell infiltration. Also, the cytokine is a potent chemotactic agent for human polymorphonuclear leukocytes while inducing little or no chemokinesis or an oxidative burst in human neutrophils in vitro, which conditions reflect the influence of a cytokine involved in mobilization by the mammalian host against an invasive stimulus. While the full and exact role played by the present inflammatory cytokine is unclear, it is theorized that the cytokine in conjunction with other factors previously identified and those yet to be elucidated, functions as part of a communication system between the immune system of the host and other body tissues and organs.

The ability of the present inflammatory cytokine to bind to heparin gave rise to the consideration that the cytokine might correspond to certain heparin-binding growth factors such as FGF or PDGF. However, data indicating that the inflammatory cytokine is not mitogenic for smooth muscle cells suggests a distinction from these known growth factors. Accordingly, what is certain at this time, is that the cytokine of the present invention participates in the development of the inflammatory response that is known to be a part of host responses such as to invasion.

The present inflammatory cytokine has been confirmed to comprise a protein that possesses a molecular mass of approximately 6,000 daltons on NaDodSO₄-PAGE and fractionates from a gel filtration column with an apparent molecular mass of approximately 10,000 daltons. The cDNA for MIP-2 has been cloned and predicts a mature protein of 74 amino acids in length with a predicted molecular weight of 7,908. In contrast to MIP-1 and cachectin/TNF, MIP-2 is cationic and does not bind to an anion exchange column equilibrated at pH 8.0. In addition, the determination of the N-terminal partial amino acid sequence and the full sequence of the mature protein confirms that the specific protein structure of the present inflammatory cytokine differs from that of other known factors. Accordingly, both structural and functional distinctions between the present inflammatory cytokine and the known factors of the prior art exists as is confirmed by the data set forth in Example 1.

More particularly, the inflammatory cytokine of the present invention possesses certain other characteristics in conjunction with those outlined above, in that it is capable of binding to heparin at high salt concentrations, e.g. approximately 0.7 M, and demonstrates colony stimulating factor activity. The cytokine is also distinctive in those activities that it lacks, such as its inability to suppress the anabolic enzyme lipoprotein lipase (LPL), to cause the cytotoxicity of cachectin/TNF-sensitive L929 cells, stimulate the blastogenesis of endotoxin-resistant C3H/HeJ thymocytes or to induce the production of cachectin/TNF by primary thioglycollate-elicited mouse macrophage cells. All of these latter activities are exhibited by the other known macrophage-derived mediator factors whose general characteristics and activities have identified them as participants in the host response to invasion. In addition, the present inflammatory cytokine is distinguishable from other factors such as MIP-1 by its inability either to induce fever in rabbits, or to induce superoxide formation or respiratory burst in human neutrophils.

The activity profile presented above accordingly distinguishes the present inflammatory cytokine from those known factors and confirms in conjunction with the amino acid sequencing data presented herein, that the present inflammatory cytokine is indeed distinct from the other macrophage-derived mediator factors.

As stated earlier, the primary amino acid sequence shown in FIG. 2 and the full sequence shown in FIG. 7 are only illustrative, and similar sequences may result in proteins which have substantially equivalent or enhanced activity. These modifications may be deliberate, for example, such as modifications obtained through site-directed mutagenesis, or may be accidental, such as those obtained through mutations in hosts which are MIP-2 producers. All of those modifications are included in the present invention, as long as the MIP-2 activity, as defined above, is retained. Accordingly, the definition of MIP-2 as stated herein and elsewhere in the specification includes proteins having an amino acid sequence substantially equivalent to that in FIGS. 2 and 7 as well as other substantially homologous analogs and allelic variations within its scope.

The preparation of the inflammatory cytokine was discussed in brief earlier herein, and is confirmed to be capable of proceeding in the instance of the native material by the initiation of the incubation of a variety of cells with stimulator materials from invasive stimuli. In particular, the cell line RAW 264.7 may be utilized to initiate the production of the material from which the inflammatory cytokine may be isolated. The murine macrophage cell line RAW 264.7 has facilitated the isolation of the inflammatory cytokine in quantities large enough to permit analysis and purification. Naturally, other cell lines or other sources for the development of either the material from which the inflammatory cytokine is thereafter isolated, or the inflammatory cytokine itself, are contemplated herein and the present invention is accordingly not limited.

As discussed earlier herein, alternate means such as by genetic replication which may be conducted in accordance with many of tohe generic principles of recombinant technology that are well known in the art, are contemplated herein in accordance with the present invention.

Accordingly, MIP-2 nucleic acid sequences may be obtained from the deduced amino acid sequence by recombinant DNA methods, such as by screening reverse transcripts of mRNA, or by screening genomic libraries from any cell. The DNA may also be obtained by synthesizing the DNA using commonly available techniques and DNA synthesizing apparatus. Synthesis may be advantageous because unique restriction sites may be introduced at the time of preparing the DNA, thereby facilitating the use of the gene in vectors containing restriction sites not otherwise present in the native source. Furthermore, any desired site modification in the DNA may be introduced by synthesis, without the need to further modify the DNA by mutagenesis.

A general procedure for isolating DNA encoding the present inflammatory cytokine from human, murine, or other sources is to construct a cDNA library from mRNA isolated from the appropriate cells or tissue; and screen with labeled DNA probes encoding portions of the polypeptide chain in order to detect clones in the cDNA library that contain homologous sequences. Alternatively, one may isolate the DNA by polymerase chain reaction (PCR) amplification of the cDNA (from mRNA) and subclone and screen with labeled DNA probes; and then analyze the clones by restriction enzyme analysis and nucleic acid sequencing so as to identify full-length clones. If full-length clones are not present in the library, appropriate fragments from the various clones may be recovered and ligated at restriction sites common to the clones to assemble a clone encoding a full-length molecule.

A suitable and preferred DNA probe is set forth in the accompanying examples. Any sequences missing from the 5' end of the MIP-2 cDNA may be obtained by the 3! extension of the synthetic oligonucleotides complementary to MIP-2 sequences using mRNA as a template (so-called primer extension), or homologous sequences may be supplied from known cDNAs derived from murine sequences as shown in FIG. 7. This will be more particularly described in Example 2; however, it is realized that once being provided with intron-free DNA encoding murine MIP-2 and its leader sequences as described herein, one of ordinary skill in the art would recognize that other precisely hybridizing probes may be prepared from the described sequences in order to readily obtain the desired gene.

Vectors are used to simplify manipulation of the DNA which encodes the MIP-2 polypeptide, either for preparation of large quantities of DNA for further processing (cloning vectors) or for expression of the MIP-2 polypeptide (expression vectors). Vectors comprise plasmids, viruses (including phage), and integratable DNA fragments, i.e., fragments that are integratable into the host genome by recombination. Cloning vectors need not contain expression control sequences. However, control sequences are needed in an expression vector, and these control sequences include transcriptional and translational control sequences such as a transcriptional promoter, an optional operator sequence to control transcription, a sequence encoding suitable ribosome binding sites (for prokaryotic expression), and sequences which control termination of transcription and translation. The expression vector should preferably include a selection gene to facilitate the stable expression of MIP-2 and/or to identify transformants. However, the selection gene for maintaining expression can be supplied by a separate vector in cotransformation systems using eukaryotic host cells.

For expression suitable vectors generally will contain replicon (origins of replication, for use in non-integrative vectors) and control sequences which are derived from species compatible with the intended expression host. By the term "replicable" vector as used herein, it is intended to encompass vectors containing such replicons as well as vectors which are replicated by integration into the host genome. Cells are then transformed or transfected with vectors containing MIP-2 encoding DNA and are now identified as transformed host cells. MIP-2 expressed from these transformed hosts will be either deposited intracellularly or secreted into the periplasmic space or the culture supernatant, depending upon the host cell selected and the presence of suitable processing signals in the expressed peptide, e.g. homologous or heterologous signal sequences.

Suitable host cells for expression can be prokaryotic or eukaryotic cells. Prokaryotes include Gram negative or Gram positive organisms, for example *E. coli* or *Bacillus subtilis*. Eukaryotic cells include yeast, baculovirus or higher eukaryotic cells such as established cell lines of mammalian origin.

Expression vectors for host cells ordinarily include an origin of replication (unless it is an integrating vector), a promoter located upstream from the MIP-2 coding sequence, together with a ribosome binding site, a polyadenylation site, and a transcriptional termination sequence. Those of ordinary skill will appreciate that certain of these sequences are not required for expression in certain hosts. A non-integrating expression vector for use with microbes need only contain an origin of replication recognized by the host, a promoter which will function in the host and a selection gene.

An expression vector is constructed according to the present invention so that the MIP coding sequence is located in the vector with the appropriate regulatory sequences, the positioning and orientation of the coding sequence with respect to the control sequences being such that the coding sequence is transcribed and translated under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site. For expression of MIP-2 in prokaryotes and yeast, the control sequences will necessarily be heterologous to the coding sequence. If the host cell is a prokaryote, it is also necessary that the coding sequence be free of introns (e.q., cDNA). If the selected host cell is a mammalian cell, the control sequences can be heterologous or homologous to the MIP coding sequence, and the coding sequence can either be genomic DNA containing introns or cDNA.

Expression vectors must contain a promoter which is recognized by the host organism. Promoters commonly known and available which are used in prokaryotic recombinant DNA expression include the β-lactamase (penicillinase) and lactose promoter systems, a tryptophan (trp) promoter system and the tac promoter. While these are commonly used, other known microbial promoters are suitable.

In addition to prokaryotes, eukaryotic cells such as yeast may be transformed with MIP-2 encoding vectors. Yeast vectors generally will contain an origin of replication or an autonomously replicating sequence (ARS), (if non-integrating) a promoter, DNA encoding MIP-2, sequences for polyadenylation and transcription termination, and a selection gene.

Of particular interest to the present invention are yeast species within the genera Pichia, Kluyveromyces, Saccharomyces, Schizosaccharomyces and Candida. Of particular interest are the Saccharomyces species *S. cerevisiae*, *S. carlsbergensis*, *S. diastaticus*, *S. douglasii*, *S. kluyveri*, *S. norbensis*, and *S. oviformis*. Species of particular interest in the genus *Kluyveromyces* include *K. lactis*, and in the genus *Pichia* include *P. pastoris*. Since the classification of yeast may change in the future, for the purposes of this invention, yeast shall be defined as described in *Biology and Activities of Yeast* (F. A. Skinner, S. M. Passmore and R. R. Davenport, eds. 1980) (SOC. APP. BACTERIOL. SYMP. SERIES NO. 9). In addition to the foregoing, those of ordinary skill in the art are presumably familiar with the biology of yeast and the manipulation of yeast genetics. See, e.g. *Biochemistry and Genetics of Yeast* (M. Bacila, B. L. Horecker and A. O. M. Stoppani eds. 1978); *The Yeasts* (A. H. Rose and J. S. Harrison eds., 2nd ed., 1987); *The Molecular Biology of The Yeast Saccharomyces* (Strathern et al. eds. 1981). The disclosures of the foregoing references are incorporated herein by reference.

Suitable promoter sequences in yeast vectors include the promoters for the glycolytic enzymes such as enolase, 3-phosphoglycerate kinase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which have the additional advantage of transcription controlled by growth conditions are the promoter regions for alcohol dehydrogenase 1 or 2, isocytochrome C, acid phosphatase, as well as enzymes responsible for maltose and galactose utilization.

Higher eukaryotic cell cultures may be used, whether from vertebrate or invertebrate cells, including insects, and the procedures of propagation thereof are known. See, for example, *Tissue Culture*, Academic Press, Kruse and Patterson, editors (1973).

Suitable host cells for expressing MIP-2 in higher eukaryotes include: monkey kidney CVI line transformed by SV40 (COS-7, ATCC CRL 1651); baby hamster kidney cells (BHK, ATCC CRL 10); Chinese hamster ovary-cells-DHFR (described by Urlaub and Chasin, PNAS (USA) 77:4216 (1980)); mouse Sertoli cells (TM4, Mather, J. P., *Biol. Reprod.* 23:243–251 (1980)); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060652, ATCC CCL 51); rat hepatoma cells (HTC, M1, 54, Baumann, M., et al., *J. Cell Biol.* 85:1–8 (1980)) and TRI cells (Mather, J. P., et al., *Annals N.Y. Acad. Sci.* 383:44–68 (1982)). Commonly used promoters are derived from polyoma, adenovirus 2, and simian virus 40 (SV40). It will be appreciated that when expressed in eukaryotic rather than prokaryotic cells, the recombinant MIP-2 may have higher molecular weight due to glycosylation. It is therefore intended that partially or completely glycosylated forms of MIP-2 having molecular weights greater than the predicted molecular weight of 7.908 are within the scope of this invention as well as its unglycosylated forms.

A number of prokaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Pub. Nos. GB 2,121,054; GB 2,008,123; GB 2,007,675; and European Pub. No. 103,395. Preferred prokaryotic expression systems are in *E. coli*.

Other preferred expression vectors are those for use in eukaryotic systems. An exemplary eukaryotic expression system is that employing vaccinia virus, which is wellknown in the art. See, e.g., Macket et al. (1984) *J. Virol.* 49:857; "DNA Cloning," Vol. II, pp. 191–211, supra; PCT Pub. No. WO 86/07593. Yeast expression vectors are known in the art. See, e.g., U.S. Pat. Nos. 4,446,235; 4,443,539; 4,430,428; see also European Pub. Nos. 103,409; 100,561; 96,491. Another preferred expression system is vector pHS1, which transforms Chinese hamster ovary cells. See PCT Pub. No. WO 87/02062. Mammalian tissue may be cotransformed with DNA encoding a selectable marker such as dihydrofolate reductase (DHFR) or thymidine kinase and DNA encoding MIP-2.

If wild type DHFR gene is employed, it is preferable to select a host Cell which is deficient in DHFR, thus permitting the use of the DHFR coding sequence as marker for successful transfection in hgt medium, which lacks hypoxanthine, glycine, and thymidine. An appropriate host cell in this case is the Chinese hamster ovary (CHO) cell line deficient in DHFR activity, prepared and propagated as described by Urlaub and Chasin, 1980, *Proc. Nat. Acad. Sci.* (USA) 77: 4216. Expression vectors derived from baculovirus for use in insect cells are known and available in the art. See Lucklow and Summers, *Biotechnology*, 6, p. 47–55.

Depending on the expression system and host selected, MIP-2 is produced by growing host cells transformed by an exogenous or heterologous DNA construct, such as an expression vector described above and in Example 2 herein, under conditions whereby the MIP-2 protein is expressed. The MIP-2 is then isolated from the host cells and purified. If the expression system secretes MIP-2 into growth media, the protein can be purified directly from cell-free media. If the MIP-2 protein is not secreted, it is isolated from cell lysates. The selection of the appropriate growth conditions and recovery methods are within the skill of the art.

The recombinantly-made MIP-2 may be recovered from transformed cells in accordance with known procedures. Preferably, an expression vector will be used which provides for secretion of MIP-2 from the transformed cells; thus the cells may be separated by centrifugation. MIP-2 is typically purified by general protein purification techniques, including, but not limited to, size exclusion, ion-exchange chromatography, HPLC, and the like.

Once a coding sequence for MIP-2 has been prepared or isolated, it can be cloned into any suitable vector and thereby maintained in a composition of cells which is substantially free of cells that do not contain a MIP-2 coding sequence (e.g., free of other library clones). Numerous cloning vectors are known to those of skill in the art. Examples of recombinant DNA vectors for cloning and host cells which they can transform include the various bacteriophage lambda vectors (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), actinophage, φC31 (Streptomyces), YIp5 (Saccharomyces), YCp19 (Saccharomyces), YEp24 (Saccharomyces), pCl/1 (Saccharomyces), XRp17 (Saccharomyces), and bovine papilloma virus (mammalian cells). See qenerally, DNA Cloning: Vols. I & II, supra; T. Maniatis et al., supra; B. Perbal, supra; Botstein et al. (1979) GENE 8: 17–24; Brake et al. (1984) PROC. NATL. ACAD. SCI. USA 81: 4642–4646; Stnichcomb et al. (1982) J. MOL. BIOL. 158: 157.

Alternatively MIP-2 may be made by conventional peptide synthesis, for instance, by using the principles of the Merrifield synthesis and using commercial automatic apparatus designed to employ the methods of the Merrifield synthesis. Peptides prepared using conventional peptide synthesis may be purified using conventional affinity chromatography, gel filtration and/or RP-HPLC.

It is further intended from the nucleotide sequences that MIP-2 analogs are within the scope of the present invention. Analogs, such as fragments, may be produced, for example, by pepsin digestion of MIP-2. Other analogs, such as muteins, can be produced by standard site-directed mutagenesis of MIP-2 coding sequences. Analogs exhibiting "MIP-2 activity" may be identified by known in vivo and/or in vitro assays.

As mentioned above, a DNA sequence encoding MIP-2 can be prepared synthetically rather than cloned. The DNA sequence can be designed with the appropriate codons for the MIP-2 amino acid sequence. In general, one will select preferred codons for the intended host if the sequence will be used for expression. The complete sequence is assembled from overlapping oligonucleotides prepared by standard methods and assembled into a complete coding sequence. See, e.g., Edge Nature 292:756 (1981); Nambair, et al. Science 223:1299 (1984); Jay et al. *J. Biol. Chem.* 259:6311 (1984).

Synthetic DNA sequences allow convenient construction of genes which will express MIP-2 analogs or "muteins". Alternatively, DNA encoding muteins can be made by site-directed mutagenesis of native MIP-2 genes or cDNAs, and muteins can be made directly using conventional polypeptide synthesis.

Site-directed mutagenesis is generally used to create analogs from a complete coding sequence. Site-directed mutagenesis is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

A general method for site-specific incorporation of unnatural amino acids into proteins is described in Christopher J. Noren, Spencer J. Anthony-Cahill, Michael C. Griffith, Peter G. Schultz, SCIENCE 244:182–188 (April 1989). This method may be used to create analogs with unnatural amino acids.

The inflammatory cytokine in accordance with the present invention was isolated and analyzed in mice as set forth in Example 1. Human inflammatory cytokine (MIP-2) is presumably similar to mouse MIP-2, since the mouse MIP-2 has an effect upon human neutrophils. As disclosed herein, this activity of the inflammatory cytokine may be harnessed by administering the inflammatory cytokine to the situs of tissue infection to promote the delivery of neutrophils to that location.

As discussed earlier, the inflammatory cytokine or its binding partner(s) or other ligands or agents exhibiting either mimicry or antagonism to the cytokine or control over its production, may be prepared in pharmaceutical compositions, with a suitable carrier and at a strength effective for administration by various means to a patient having a tissue infection or other pathological derangement, for the treatment thereof. A variety of administrative techniques may be utilized, among them topical applications as in ointments or on surgical and other topical appliances such as, surgical sponges, bandages, gauze pads, and the like. Also, such compositions may be administered by parenteral techniques such as subcutaneous, intravenous and intraperitoneal injections, including delivery in an irrigation fluid used to wash body wound areas, catheterizations and the like. Average quantities of the inflammatory cytokine may vary and in particular should be based upon the recommendations and prescription of a qualified physician or veterinarian.

Also, antibodies including both polyclonal and monoclonal antibodies, and drugs that modulate the production or activity of the inflammatory cytokine may possess certain therapeutic applications and may thus be utilized for the purpose of treating the effects of post infection attributable the action of the inflammatory cytokine, such as inflammation and fever. In particular, the inflammatory cytokine may be used to produce both polyclonal and monoclonal antibodies to itself in a variety of cellular media, by known techniques such as the hybridoma technique utilizing, for example, fused mouse spleen lymphocytes and myeloma cells.

The general methodology for making monoclonal antibodies by hybridomas is well known. Immortal, antibodyproducing cell lines can also be created by techniques other than fusion, such as direct transformation of *B lymphocytes* with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against MIP-2 peptides can be screened for various properties; i.e., isotype, epitope, affinity, etc. Of particular interest are monoclonal antibodies that neutralize the activity of MIP-2. Such monoclonals can be readily identified in MIP-2 activity assays. High affinity antibodies are also useful in innnunoaffinity purification of native or recombinant MIP-2.

The resulting antibodies could also be prepared in a suitable pharmaceutical composition and administered to avert or treat the undesired condition. The exact quantities, intervals of administration and admimistrative techniques respecting such pharmaceutical compositions may vary in accordance with those known in the medical arts, and upon the specific instruction of a qualified physician or veterinarian.

The present invention also relates to a variety of diagnostic applications, including methods for detecting the presence of invasive stimuli by reference to their ability to elicit the activities which are affected by the present inflammatory cytokine. As mentioned earlier, the inflammatory cytokine can be used to produce antibodies to itself by a variety of known techniques, and such antibodies could then be isolated and utilized as in tests for the presence of the inflammatory cytokine in suspect mammalian hosts.

Antibody(ies) to the inflammatory cytokine can be produced and isolated by standard methods including the well known hybridoma techniques. For convenience, the antibody(ies) to the inflammatory cytokine will be referred to herein as $Ab_1$ and antibody(ies) raised in another species as $Ab_2$.

The presence of inflammatory cytokine activity in mammals can be ascertained by the usual immunological procedures applicable to such determinations. A number of useful procedures are known. Three such procedures which are especially useful utilize either the inflammatory cytokine labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Cyt" stands for the inflammatory cytokine:

A. $Cyt^* + Ab_1 = Cyt^*ab_1$

B. $Cyt + Ab^* = CytAb_1^*$

C. $Cyt + Ab_1 + Ab_2^* = CytAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the inflammatory cytokine forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-inflammatory cytokine antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The inflammatory cytokine or its binding partner(s) can also be labeled with a radioactive element or with an enzyme. The radioactive label can be detected by amy of the currently available counting procedures. The preferred isotope may be selected from $^{14}C$, $^{131}I$, $^{3}H$, $^{125}I$ and $^{35}S$.

Enzyme labels are likewise useful, and can be detected by any of the presently utilized colorimetric, spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the inflammatory cytokine may be radiolabeled, after which binding studies would be carried out using for example, recently differentiated neutrophils. Solutions would then be prepared that contain various quantities of labeled and unlabeled inflammatory cytokine and cell samples would then be inoculated and thereafter incubated. The resulting cell monolayers are then washed, solubilized and then counted in a gamma counter for a length of time sufficient to yield a standard error of <5%. This data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

In a further embodiment of this invention, commercial test kits suitable for use by a medical specialist may be prepared to determine the presence or absence of inflammatory cytokine in a suspected mammalian host. In accordance with the testing techniques discussed above, one class of such kits will contain at least the labeled inflammatory cytokine or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the reaction of a mammalian host to invasive stimuli, comprising:

(a) a predetermined amount of at least one labeled immunochemically reactive component obtained by the direct or indirect attachment of the present inflammatory cytokine or a specific binding partner thereto, to a detectable label;

(b) other reagents; and (c) directions for use of said kit.

More specifically, the diagnostic test kit may comprise:

(a) a known amount of the inflammatory cytokine as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "andwich", "double antibody", etc.), and comprises:

(a) a labeled component which has been obtained by coupling the inflammatory cytokine to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the inflammatory cytokine and a specific binding partner thereto.

In accordance with the above, an assay system for screening potential drugs effective to modulate the synthesis, release, or activity of the inflammatory cytokine may be prepared. In a first procedure, the test drug could be administered to a stimulated macrophage sample to determine its effect upon the production of the inflammatory cytokine. In an alternate procedure, the inflammatory cytokine may be introduced into a cellular test system such as neutrophils, and the prospective drug may also be introduced into the resulting cell culture, and the culture thereafter examined to observe any changes in the activity of the inflammatory cytokine, due either to the addition of the prospective drug alone, or due to the effect of added quantities of the known inflammatory cytokine.

The following examples set forth the details of the isolation and identification of the present inflammatory cytokine, the observations noted as to its activity, defining both the distinctions and similarities in activity between the present inflammatory cytokine and those factors identified earlier both by applicants and by others in the field, and the cloning, sequencing and expression of the cytokine MIP-2. Naturally, the specific materials and techniques set forth hereinafter are exemplary only and may vary, so that the following is presented as illustrative but not restrictive of the present invention.

EXAMPLE 1

The following experiments were conducted to identify and characterize the inflammatory cytokine of the present invention. Initially, the mediator subtance was cultured, the inflammatory cytokine was isolated and its structure then partially determined, after which a battery of tests were conducted in an effort to elucidate its activities, and where possible, to establish or refute identity with other known macrophage-derived factors.

MATERIALS AND METHODS

Materials—Supernatants from COS cells transfected with plasmid containing the hamster or human gro gene or control plasmid alone were provided by A. Anisowicz and R. Sager. Partially purified human NAP-1 protein was a gift from J. Van Damme and purified human NAP-1 protein was given by T. Yoshimura and E. Leonard. All other reagents were obtained from Sigma (St. Louis, MO).

Animals—C3H/HeN mice were obtained from Charles River (Kingston, NY). Mice of the endotoxin-resistant C3H/HeJ strain were obtained from Jackson Laboratories (Bar Harbor, ME).

Cell Culture—The mouse macrophage cell line RAW 264.7 and the cachectin/TNF-sensitive cell line L929 were obtained from American Type Culture Collection (Rockville, MD) and maintained in RPMI 1640 and Dulbecco's modified MEM ((DMEM) GIBCO, Grand Island, NY), respectively. Both media were supplemented with 20 mM Hepes and 10% fetal bovine serum (Hyclone, Logan, UT).

For the production of stimulated RAW 264.7 supernatants, cells were grown in 150 mm tissue culture dishes (Falcon) in RPMI plus 10% fetal bovine serum until they reached confluency. The cells were washed five times in Hanks' balanced salt solution and the medium was replaced with serum-free RPMI supplemented with 1 µg/ml of lipopolysaccharide (LPS W, $E.\ coli$ 0127:B8, Difco, Detroit, MI). The cells were incubated at 37° C. for 16–18 hours and the supernatants filtered through 0.22 µm filters.

Purification of MIP-2—MIP-2 was purified using methodology previously described for MIP-1 (S. D. Wolpe, G. Davatelis, B. Sherry, B. Beutler, D. G. Hesse, H. T. Nguyen, L. L. Moldawer, C. F. Nathan, S. F. Lowry, & A. Cerami (1988), J. EXP. MED., 167:570–581). The degree of purification was followed by sodium dodecyl sulfate (NaDodSO$_4$-PAGE) with silver staining. In brief, two liters of conditioned supernatant from endotoxin-stimulated RAW 264.7 cells were concentrated and diafiltrated against 20 mM Tris-HCl buffer, pH 8.0, and applied to a Mono Q 10/10 (anion exchange) column (Pharmacia LKB Biotechnology, Rahway, NJ). Greater than 90% of the MIP-2 was observed not to bind to the column and was recovered in the effluent. Peak MIP-2 containing fractions were applied to a heparin-conjugated Sepharose (Pharmacia LKB) column equilibrated with 20 mM Tris-HCl buffer, pH 8.0, and eluted with a 0–2 M NaCl linear gradient in the same buffer. MIP-2 eluted at approximately 0.75 M NaCl. Peak fractions were concentrated in a Centricon ultrafiltration device with a 3,000 dalton molecular weight cutoff (Amicon Corp., Danvers, MA) and applied to a Superose 12 (gel filtration [Pharmacia LKB]) column equilibrated with 100 mM ammonium acetate. From two liters of RAW 264.7 conditioned medium (which equalled approximately 100 mg total protein), a quantity of 0.5 mg of MIP-2 was generally isolated as assessed by Bradford protein assay (Biorad, Rockville Center, NY) using bovine gamma globulin as standard. By comparison, approximately 2 mg of MIP-1 and 1 mg of cachectin/TNF could be purified from a like batch of conditioned medium.

Immunoblot Analysis—Antisera to MIP-2 were produced in rabbits injected once subcutaneously with 10 µg of purified protein emulsified in complete Freund's adjuvant, and once one month later with 10 µg of purified protein in incomplete Freund's adjuvant. Antisera were collected one week after the second immunization. Approximately 50 ng of pure MIP-2 or NAP-1 protein, or roughly equivalent amounts of human or hamster gro protein from the serum-free supernatants of COS cells transfected with the appropriate vector, were subjected to NaDodSO$_4$-PAGE in 10–18% linear gradient gels and transferred to nitrocellulose using a transblot apparatus (Biorad). Blots were blocked in 5% dry milk (Alba) for 1–2 hrs. and incubated in antiserum diluted 1:100 for 1 hr. at room temperature. The blots were washed three times in phosphate-buffered saline containing 0.05% Tween 20 and 0.05% thimerosal and bound antibody was detected with an alkaline phosphatase-conjugated second antibody (Promega Biotec, Madison, WI).

PMN Chemotaxis and Activation—The assay for chemotaxis was conducted as previously described (S. D. Wolpe, G. Davatelis, B. Sherry, B. Beutler, D. G. Hesse, H. T. Nguyen, L. L. Moldawer, C. F. Nathan, S. F. Lowry, & A. Cerami (1988), J. EXP. MED., 167:570–581). In brief, chemotaxis was assayed by placing 25 µl of chemoattractant (fMet-Leu-Phe [$10^{-8}$ M], MIP-2 or buffer], Gey's balanced salt solution, pH 7.4 and 2% BSA]) in the bottom wells, and the top wells were filled with 45 µl of buffer containing $1.1 \times 10^4$ PMN's (isolated by Ficoll-Hypaque density gradient centrifugation and dextran sedimentation). The two wells were separated by a cellulose nitrate membrane with a 3 µM pore size (SM 11302; Sartorius Balances, Westbury, NY). Chambers were incubated at 37° C. in a humidified 5% carbon dioxide, 95% room air chamber for 45 minutes. Membranes were removed and stained and the number of PMN's migrating into the membrane was counted every 10 µM up to 130 µM using an automated Optomax Imaging System (Optomax, Inc., Hollis, NH). Random migration was also determined under conditions where the gradient of chemotactic agent was abolished by including equal concentrations in the upper and lower chambers.

The ability of MIP-2 to elicit the release of $H_2O_2$ from adherent PMN's was assayed as previously described (S. D. Wolpe, G. Davatelis, B. Sherry, B. Beutler, D. G. Hesse, H. T. Nguyen, L. L. Moldawer, C. F. Nathan, S. F. Lowry, & A. Cerami (1988), J. EXP. MED., 167:570–581).

RESULTS

Purification of MIP-2—As judged from silver-stained NaDodSO$_4$-PAGE gels, more than 90% of MIP-2 remained in the effluent of the Mono Q column (FIG. 1). This one-step purification step was sufficient to remove contaminating MIP-1 and cachectin/TNF. As previously shown (Wolpe, et al., supra), these two proteins bind to the Mono Q column under these loading conditions and elute at approximately 0.37 M NaCl. Two successive steps of heparin-affinity chromatography and gel filtration were sufficient to purify MIP-2 protein to homogeneity (FIG. 1). MIP-2 eluted from heparin-Sepharose column at approximately 0.75 M NaCl and migrated with an apparent molecular weight of 10,000 daltons on gel filtration.

Analysis of partial NH$_2$-terminal amino acid sequence data of purified MIP-2 (FIG. 2) revealed a unique sequence. Comparison with other sequences present in the Dayhoff bank using the d-FAST-P program (D. J. Lipman and W. R. Pearson (1985), SCIENCE, 227:1435–1441) revealed similarity to a family of proteins with sequence relatedness to platelet factor 4. FIG. 2 depicts the partial $NH_2$-terminal amino acid sequences of MIP-2 and various members of this family aligned by a conserved cysteine residue. FIG. 3 depicts a comparison of the percent sequence identify over the region corresponding to the partial amino acid sequence obtained for MIP-2. The closest relationship observed for MIP-2 was with the predicted amino acid sequence for the gro gene product. The MIP-2 sequence is 62.5% identical with human gro and 68.7% identical with hamster gro. This relationship increases to 88% in both cases when amino acid changes which could result from a single base change are taken into consideration.

The similarity in amino acid sequence between MIP-2 and gro suggested that MIP-2 could be the murine equivalent of qro. The predicted murine KC gene product ("KC"), however, showed a closer relationship (65.6% identity to human qro and 81.2% identity to hamster qro for KC versus 62.5% and 68.7% respectively for MIP-2) when compared over the same region as the partial sequence for MIP-2. Similar results were obtained when the comparisons were conducted over the entire sequence. KC was 68% identical to human gro and 85% to hamster gro. Human and hamster gro were 68% identical when compared to each other over their entire sequence.

Figures 4A, 4B:
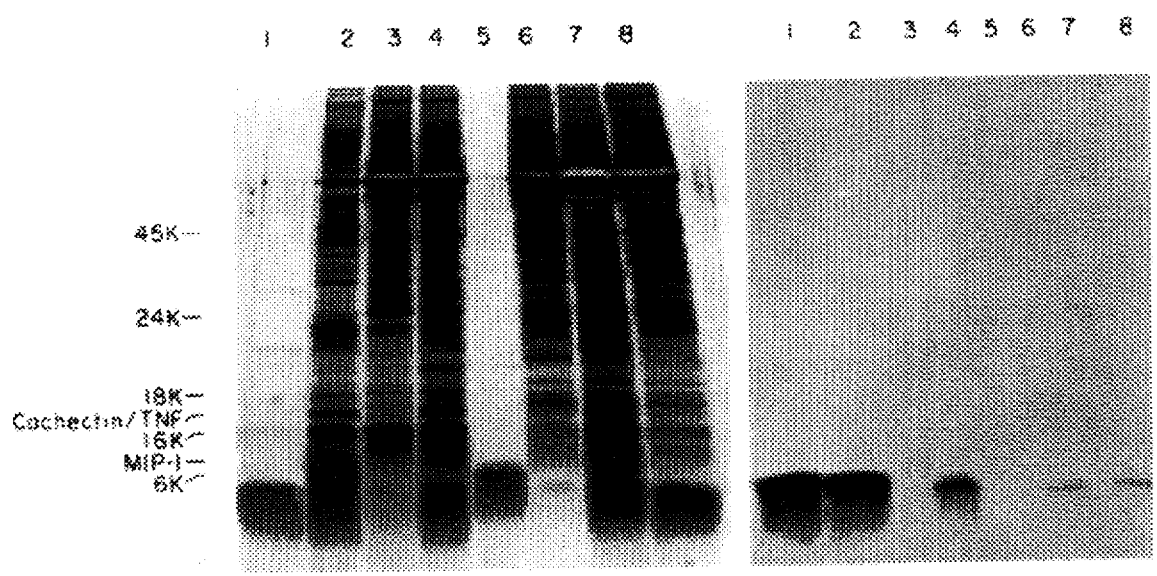
FIG. 4 depicts an immunoblot analysis characterizing the relationship between MIP-2 and other members of the platelet factor 4 family. (A) Silver stain of duplicate of gel used for immunoblot of MIP-2. (B) Immunoblot of MIP-2: Lane 1—purified MIP-2; Lane 2—supernatant from endotoxin-stimulated RAW 264.7 cells; Lane 3 supernatant from non-stimulated thioglycollate-elicited mouse peritoneal macrophages; Lane 4—supernatant from endotoxin-stimulated, thioglycollate-elicited mouse peritoneal macrophages; Lane 5—purified NAP-1 protein; Lane 6—supernatant from COS cells transfected with plasmid alone; Lane 7—supernatant from COS cells transfected with plasmid containing the human gro gene; Lane 8—supernatant from COS cells transfected with plasmid containing the hamster gro gene. Lanes 7 and 8 are reversed in the immunoblot (4b).

Immunoblot Analysis—In order to further characterize the relationship between MIP-2 and the other members of the platelet factor 4 family, a rabbit polyclonal antiserum was raised against MIP-2. The antiserum reacted monospecifically against serum-free supernatants from endotoxin-stimulated RAW 264.7 cells or thioglycollate-elicited mouse macrophages but did not recognize any proteins in supernatants from unstimulated cells. An example of such a blot with antibody against MIP-2 is shown in parts a and b of FIG. 4. Preimmune serum also showed no reactivity. In particular, antiserum to MIP-2 did not cross-react with MIP-1 or cachectin/TNF (see, for example, lane 2 of FIG. 4). Rabbit anti-MIP-2 cross-reacted weakly with human and hamster gro but did not cross-react with purified human NAP-1 protein (FIG. 4). Similarly, no cross-reaction was seen with partially purified human NAP-1 from another laboratory (supplied by J. Van Damme). In addition, the human myelomonocytic cell line HL60 secreted a cross-reacting protein after stimulation with $10^{-7}$ M phorbol myristic acid, further suggesting that the lack of reactivity of anti-MIP-2 antibody with the human NAP-1 protein is due to lack of immunological relatedness rather than to species specificity. The nature of the cross-reacting material from HL60 cells is under investigation.

PMN Chemotaxis and Activation—Because other members of the PF4 family have been shown to be chemotactic for and to activate PMN's, the effect of MIP-2 on these cells was studied. MIP-2 was significantly chemotactic for human PMN's at 10 ng/ml and was more chemotactic for PMN's than fMet-Leu-Phe at concentrations greater than 100 ng/ml (FIG. 5). When equal concentrations of MIP-2 were added to both sides of the membrane, no increase in migration was observed. Thus, the activity of MIP-2 at the concentrations tested appears to be due to stimulation of directed migration of the cells rather than enhancement of random migration.

PMN's did not undergo an oxidation burst (as measured by production of hydrogen peroxide) when treated with concentrations of MIP-2 ranging from 10 ng to 1 µg per ml.

In addition to these in vitro assays, MIP-2 was tested in vivo by injection of 100 ng into the footpads of endotoxin-resistant C3H/HeJ mice. This injection induced a leukocyte infiltrate similar in magnitude to that previously shown for MIP-1.

DISCUSSION

MIP-2 has a molecular mass of approximately 6,000 daltons on $NaDodSO_4$-PAGE and fractionates from a gel filtration column with an apparent molecular mass of approximately 10,000 daltons. In contrast to MIP-1 or cachectin/TNF, MIP-2 is cationic and does not bind to an anion exchange column equilibrated at pH 8.0. This property made separation of these activities and subsequent purification of MIP-2 relatively straightforward. After removal of the majority of contaminating proteins by anion exchange, MIP-2 was purified to homogeneity by sequential heparin affinity chromatography eluting at approximately 0.75 M NaCl and gel filtration.

MIP-2 is an extremely active chemotactic agent but induces little or no chemokinetic activity at the doses tested. At 10 ng/ml ($1.7 \times 10^{-9}$ M), MIP-2 is significantly chemotactic for human PMN's and at concentrations greater than 100 ng/ml ($1.7 \times 10^{-8}$ M) MIP-2 exhibits a higher leukotactic index than fMet-Leu-Phe at the latter's optimum concentration of $10^{-8}$ M. Studies indicate that MIP-2 can also induce degranulation of PMN's with release of lysozyme but not β-glucuronidase. Murine MIP-2 did not, however, induce the respiratory burst in human PMN's. It is not yet clear whether this is due to species specificity or is an inherent property of the molecule.

The above effects on PMN's are similar to observations made with a protein isolated from human mononuclear cells by a number of investigators and variously referred to as "310C", "MDNCF", "MONAP", "NAF" or "GCP" [Schmid, J. & Weissmann, C. (1987) J. IMMUN. 139:250–256; Yoshimura, T., Matsushima, K., Oppenheim, J. J. & Leonard, E. J. (1987) J. IMMUN. 139:788–793; Yoshimura, T., Matsushima, K., Tanaka, S., Robinson, E. A., Appella, E., Oppenheim, J. J. and Leonard, E. J. 1987. PROC. NATL. ACAD. SCI. USA 84:923–9237; Schroder, J. M., Mrowietz, U., Morita, E. & Christophers, E. (1987) J. IMMUN. 139:3474–3483; Walz, A., Peveri, P., Aschauer, H. & Baggiolini, M. (1987) BIOCH. BIOPHYS. RES. COMM. 149:755–761; Peveri, P., Walz, A., Dewald, B. and Baggiolini, M. (1988) J. Exp. Med. 167:1547–1559; Van Damme, J., Beeumen, J. V., Opdennakker, G. and Billiau, A. (1988) J. EXP. MED. 167:1364–1376.] This protein is now known as "neutrophil activating protein-1" (NAP-1). Because of the striking similarity in properties of MIP-2 and NAP-1, the possibility was considered that MIP-2 might be the murine equivalent of NAP-1. This relationship appears not to be the case based on both sequence and immunological analyses. Comparison of the N-terminal sequence of MIP-2 with the PF-4 family using the FASTP program shows a 47% identity with NAP-1 but a 63% and 69% identity with human and hamster gro, respectively. This relationship agrees well with the immunoblotting results which demonstrated cross-reactivity with hamster and human gro but not with NAP-1 from two different laboratories.

It also appears unlikely that MIP-2 is the murine equivalent of gro because the predicted murine KC gene product shows an even higher sequence identity to gro, especially in the case of hamster gro. Applicants therefore conclude that MIP-2 is a novel gene product closely related to, but separate from, gro or KC.

It is of interest that the gro and KC genes were originally found in studies on the control of cell growth. The gro gene was isolated by differential hybridization of DNA from transformed cells [Anisowicz, A., Bardwell, L. and Sager, R. (1987) PROC. NATL. ACAD. SCI. USA 84:P7188–7192];

the KC gene was isolated by differential hybridization of DNA from cells treated with platelet-derived growth factor [Cochran, B. H., Reffel, A. C. and Stiles, C. D. (1983) CELL 333:939–947]. Transfection of cells with the gro gene does not lead to transformation, however [Anisowicz, A., Bardwell, L. and Sager, R. (1987) PROC. NATL. ACAD. SCI. USA 84:P7188–7192]. Similarly, treatment of density-arrested 3T3 fibroblasts with MIP-2 or MIP-2 plus limiting amounts of serum or plasma does not increase uptake of $^3$H thymidine.

EXAMPLE 2

The following sets forth the cloning and expression of MIP-2. The cloning of the cDNA for murine MIP-2 was as follows. A degenerate oligonucleotide probe pool corresponding to amino acids 9–14 of a partial $NH_2$-terminal sequence of MIP-2 was synthesized. This portion of the partial sequence was chosen because of its lower codon degeneracy when compared with the remainder of the sequence. The resulting probe was a 128 fold degenerate pool of oligomers 17 nucleotides in length.

A cDNA library was constructed from Poly(A)$^+$ RNA isolated from *E. coli* lipopolysaccharide-stimulated RAW 264.7 cells as taught in Davatelis et al., J. EXP. MED. 167: 1939–1941 (1988) and Sherry et al. J. EXP. MED. 168: 2251–2259 (1988). Duplicate nitrocellulose filter lifts of the plated library ($5\times10^5$ plaques) were hydbridized at 42° C. in 5×SSC, 1×Denhardt's, 20 mm sodium phosphate buffer, pH6.5, 50% formamide, 10% dextran sulfate, 0.1% SDS, 0.1 mg/ml sonicated salmon sperm DNA and $5\times10^4$ cpm per ml per degeneracy of $^{32}$P-ATP 5' end-labelled synthetic oligonucleotide probe pool. Following hybridization the filters were washed employing the TMAC washing procedure described by Wood et al. PROC. NATL. ACAD. SCI. USA 82: 1585 (1985). Plaques that were positive on duplicate filters were subjected to a second round of low density plating and screening. Four independent positive phage clones were isolated from which DNA was prepared for further analysis. cDNA inserts were excised by digestion with EcoR1 and subcloned into M13 phage vector. DNA sequencing was performed by the didioxy chain termination method of Sanger et al. PROC. NATL. ACAD. SCI. USA 74: 5463 (1977). The nucleotide sequence of one of the inserts was determined and found to encode a secreted protein that includes the amino acid sequence determined from amino terminal sequencing of purified native MIP-2. The sequence of the cDNA clone and the predicted protein sequence are shown in FIG. 7.

Construction of Expression Plasmid pYMIP400

This plasmid encodes an s-factor leader linked to the mature coding sequence of MIP-2. The MIP-2 mature coding sequence was derived from the MIP-2 cDNA determined above. The GAPDH promotor sequence, the α-factor leader sequence and the α-factor transcription terminator were derived from plasmid pGAI1, the construction of which is described in European Publication No. 324,274, published 19 Jul. 1989, the disclosure of which is incorporated herein by reference.

A BglII site was introduced by in vitro mu,tagenesis into the nucleotide sequence encoding the carboxyl terminus of MIP-2 in order to facilitate cloning into the expression vector. The mutagenic primer was:

```
            **
5' - CAAAAGATCTTGAACAAAG - 3'
```

(*denotes base changes from original cDNA sequence)

Following verification of the altered cDNA sequence, phage RF was prepared and digested with BalI and BglII. A 1966 bp fragment encoding most of the mature MIP-2 (lacking the sequence encoding 2 N-terminal and 9 C-terminal amino acids) was isolated. Plasmid pGAI1 described in European Publication No. 324,274, published 19 Jul. 1989, was digested with KpnI and ligated to the following adaptor which encodes the 3 alpha factor leader carboxyl terminal amino acids, the LysArg processing site and the first 3 amino acids of mature MIP-2.

KpnI - BalI adaptor
```
5'    CCTTGGATAAAAGAGCTGTTGTGG 3'
3' CATGGGAACCTATTTTCTCGACAACACC 5'
```

Following digestion with SalI, the following BglII—SalI adaptor was added which encodes for the 8 carboxyl terminal amino acids of MIP-2 as well as translational stop codons.

BglII - SalI adaptor
```
5' GATCTTGAACAAAGGCAAGGCTAACTGATAGCGTCG     5'
3'     AACTTGTTTCCGTTCCGATTGACTATCGCAGCAGCT 3'
```

The modified vector is gel purified and ligated to the 1966 bp BalI-BglII fragment described above, after which screening to isolate plasmid pMIP400 is conducted. The plasmid is then isolated, and its nucleotide sequence across the adaptors is verified, after which the BamH1 expression cassette from this plasmid is isolated and cloned into the BamH1 site of pAB24 to give the expression plasmid pYMIP400.

Expression of MIP-2

*S. cerevisaie* strain MB2-1 (leu2-3, leu2-112, his3-11, his3-15, ura3▲, pep4▲, CAN', cir°) is transformed with plasmid pYMIP400 by standard procedures and transformants selected for ura prototrophy. Expression is analyzed by inoculation of single colonies of individual transformants into leucine selective medium, and growing for ~48 hr. Cultures are then centrifuged, cells resuspended in medium lacking uracil and diluted 20 fold into ura selective medium. Cultures are grown for approximately 72 hr, then harvested and cell-free supernatants prepared. Conditioned medium is analyzed for the presence of MIP-2 by SDS-PAGE followed by coomassie staining and immunoblotting.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. An antibody to an inflammatory cytokine, which inflammatory cytokine elutes from a heparin affinity column in a 0–2 M NaCl gradient at 0.75 M NaCl, is cationic under physiological conditions, and is characterized by inducing localized intimation characterized by polymorphonuclear cell infiltration when administered subcutaneously and having potent in vitro chemotactic activity while inducing little or no in vitro chemokinesis in polymorphonuclear cells, while lacking the ability to suppress the activity of the anabolic enzyme lipoprotein lipase, cause the cytotoxicity of cachectin/TNF-sensitive cells, stimulate the blastogenesis of endotoxin-resistant C3H/Hel thymocytes, or induce the production of cachectin/TNF by primary thioglycollate-elicited mouse macrophage cells, which cytokine has an apparent molecular mass of approximately 6000 Daltons by SDS-PAGE, and fractionates from a gel filtration column with an apparent molecular mass of approximately 10,000 Daltons.

2. The antibody of claim 1 comprising a polyclonal antibody.

3. The antibody of claim 1 comprising a monoclonal antibody.

4. An hybridoma cell line that produces a monoclonal antibody according to claim 3.

5. The antibody of claims 1 labeled with a detectable label.

6. The antibody of claim 5 wherein the label is selected from the group consisting of an enzyme, a chemical which fluoresces, and a radioactive element.

7. The antibody of claim 1, wherein the inflammatory cytokine has partial N-terminal sequences as depicted in FIG. 6.

8. The antibody of claim 1, wherein the inflammatory cytokine has an amino acid sequence as depicted in FIG. 7.

* * * * *